United States Patent [19]

Clement et al.

[11] Patent Number: 5,066,746

[45] Date of Patent: Nov. 19, 1991

[54] PERFLUOROCYCLOBUTANE RING-CONTAINING POLYMERS

[75] Inventors: Katherine S. Clement; David A. Babb, both of Lake Jackson, Tex.; Bobby R. Ezzell, Midland, Mich.

[73] Assignee: The Dow Chemical Company, Midland, Mich.

[21] Appl. No.: 534,819

[22] Filed: Jun. 7, 1990

Related U.S. Application Data

[63] Continuation-in-part of Ser. No. 364,667, Jun. 9, 1989.

[51] Int. Cl.$^5$ .............................................. C08F 14/18
[52] U.S. Cl. .................................... 526/242; 526/243; 526/245; 526/247; 526/248; 526/250; 526/251; 526/252; 526/253; 526/255; 528/86; 568/669
[58] Field of Search ............... 526/243, 242, 245, 248, 526/250, 251, 252, 253, 255, 247; 528/86; 568/669

[56] References Cited

U.S. PATENT DOCUMENTS

| | | |
|---|---|---|
| 2,982,786 | 5/1961 | McCane . |
| 3,111,509 | 11/1963 | Folt . |
| 3,114,778 | 12/1963 | Fritz et al. . |
| 3,310,606 | 3/1967 | Fritz . |
| 3,696,154 | 10/1972 | Anderson . |

FOREIGN PATENT DOCUMENTS

| | | |
|---|---|---|
| 303292 | 2/1989 | European Pat. Off. . |
| 1126554 | 9/1968 | United Kingdom . |
| 1185564 | 3/1970 | United Kingdom . |
| 8602072 | 4/1986 | World Int. Prop. O. . |

OTHER PUBLICATIONS

Coffmann et al.; J. Amer. Chem. Soc., vol. 71 (1949), pp. 490–496.
Paleta et al., "Haloacrylic Acids VI Ethylene Glycol Bis(Trifluoroacrylate)Sb Vsy Sk", Chem Technol 1976, C23, 5–11 (1976).
A. A. Glazkov et al., Bulletin of the Academy of Sciences of the USSR, vol. 37, No. 10, part 2.
P. Tarrant et al., J. Org. Chem., vol. 31, No. 4, 1966, pp. 1143–1146.
Chemical Abstract 105: 171569h.
Chemical Abstracts 59: 8879c.
Chemical Abstracts 77: 34091k.

*Primary Examiner*—Paul R. Michl
*Assistant Examiner*—T. McDonald, Jr.

[57] ABSTRACT

The present invention is a process for preparing a polymer having perfluorocyclobutane rings by the steps of (a) contacting monomers having at least two dimerizable perfluorovinyl groups; and (b) exposing the monomers to sufficient heat and for a sufficient time that a polymer containing perfluorocyclobutane rings is formed wherein at least about 0.05 mole percent of the monomer, have at least 3 dimerizable perfluorovinyl groups and polymers prepared thereby.

18 Claims, No Drawings

PERFLUOROCYCLOBUTANE RING-CONTAINING POLYMERS

This is a continuation-in-part of U.S. application Ser. No. 364,667 now abandoned filed June 9, 1989.

This invention relates to polymerizations of perfluorovinyl compounds and to compositions containing more than one perfluorocyclobutane ring, more particularly to crosslinked polymeric compositions containing more than one perfluorocyclobutane ring.

It has long been recognized that perfluorovinyl compounds having more carbon atoms than tetrafluoroethylene are very difficult to polymerize into aliphatic chains. Such difficulties are discussed, for instance in U.S. Pat. Nos. 2,848,504 and 2,958,685; and in *J. Polymer Science*, Part 1-A, pp. 481–492 (1952) and vol. 6, pp 711–717 (1968).

Dimerization of certain perfluorovinyl compounds has been reported and is discussed, for instance, in Chambers, *Fluorine in Organic Chemistry*, John Wiley, N.Y., 1973, pp. 173-191; S. Patai, *The Chemistry of Alkenes*, Wiley Interscience Publishers, 1964, p. 779: M. Hudlicky, *Chemistry of Organic Fluorine Compounds*, 2nd ed., Halsted Press (John Wiley and Sons), 1972, p. 450; and Tarrant ed., *Fluorine Chemistry Reviews*, Vol. 2, Marcel Dekker, 1968 pp. 1-52. In general, the dimerizations are easily sterically hindered and have not been used to prepare long chain molecules. A report of dimerization linking two molecules of such compounds as perfluoropropylene and perfluoropentene-1, included speculation that the reaction could be used for perfluoroalkyl perfluorovinyl compounds wherein the alkyl radical has 1 to 20, "or even a higher number" of carbon atoms. See, McCone et al., U.S. Pat. No. 3,316,312.

Such dimerization has not previously been reported to produce compounds having more than one perfluorocyclobutane ring. In fact, few compounds having multiple perfluorinated four carbon-rings have been reported. U.S. Pat. No. 3,303,145 discloses a number of polyethers formed from cyclic fluorocarbon epoxides, which polymers can have perfluorocyclobutane rings separated by oxygen atoms. The polymers are said to have good thermal stability and chemical inertness as well as dielectric properties. Use as solvents, heattransfer media and lubricants as well as insulators in the form of films and moldings is suggested. U.S. Pat. No. 3,682,876 discloses polyperfluorocyclobutene and halogen terminated polyperfluorocyclobutadienes. The solid polyperfluorocyclobutadienes are reported to be thermally stable, chemically inert and useful as coatings, ablatives, gaskets, bearings, potting compounds and sealants. U.S. Pat. No. 3,900,380 discloses polymers prepared by coupling certain perfluoroalkyl or perfluoroalkyl ether chains with iodine terminated perfluorocyclobutanes to prepare polymers having double bonds suitable for cross linking. The liquids are reported to be useful as hydraulic fluids, and the solids as gaskets and ablatives. Certain polymers containing radical-initiated rings, assumed for steric reasons to be four-membered rings are reported by Brown et al. in *J. Polymer Sci: Part A* vol. 3, pp 1641-1660 (1965) and vol. 4, pp 131-140 (1966). None of these reported polymers having perfluorocyclobutane rings is formed by thermal reaction of perfluorovinyl groups. Also, none has aromatic structure.

SUMMARY OF THE INVENTION

In one aspect the invention is a polymer having perfluorocyclobutane rings comprising the steps of:
(a) contacting monomers having at least two dimerizable perfluorovinyl groups; and
(b) exposing the monomers to sufficient heat and for a sufficient time that a polymer containing perfluorocyclobutane rings is formed
wherein at least about 0.05 mole percent of the monomers have at least three dimerizable perfluorovinyl groups.

In another aspect, the invention includes polymers formed by the process.

In another aspect the invention is a polymer having a backbone comprising perfluorocyclobutane rings being formed from monomers having at least two dimerizable perfluorovinyl groups per molecule wherein at least 0.05 mole percent of the monomers have at least three dimerizable perfluorovinyl groups per molecule.

DETAILED DESCRIPTION OF THE INVENTION

Polymers of the invention are formed by thermal reaction of monomers having at least two dimerizable perfluorovinyl groups such that perfluorocyclobutane groups are formed. A dimerizable perfluorovinyl group is a perfluorovinyl group which reacts with another such group to form a perfluorocyclobutane ring. Thus, resulting polymers have at least two perfluorocyclobutane groups, in particular sufficient perfluorocyclobutane groups to achieve physical and electrical properties desired for specific uses of the polymers. The term polymer is used herein to refer to any compound having at least two perfluorocyclobutane groups formed from perfluorovinyl groups, and includes oligomers which have from about 2 to about 100 repeating units and preferably have a molecular weight of from about 300 to about 30,000. It is within the scope of the present invention to form lower molecular weight oligomers useful as fluids or prepolymers and higher molecular weight polymers exhibiting general plastic properties. Within this scope and depending on the molecular structure connecting the perfluorocyclobutyl groups, the number of perfluorocyclobutane groups can vary from as few as two up to thousands. The process of forming polymers or oligomers by the process of the present invention is general and capable of forming products having wide ranges of utility. Physical and electrical properties of the resulting products are highly dependent on the choice of the molecular structure between the perfluorocyclobutane groups as well as the number of perfluorocyclobutane groups.

The relative proportion by weight of the perfluorocyclobutane groups to the other molecular components of the resulting products can vary over a wide range of from about 12 to 1 to about 0.01 to 1, preferably from about 5 to 1 to about 0.02 to 1 and most preferably from about 2 to 1 to about 0.03 to 1. High proportions of perfluorocyclobutane groups are desirable for instance, when fluorocarbon character such as low dielectric constant is beneficial in the products. Exemplary of such products are low dielectric fluids and lubricants. Medium ranges of ratios of weights of perfluorocyclobutane groups to other molecular structures of about 2 to 1 to about 1 to 4 are desirable, for instance, when higher physical strength and relatively lower dielectric constants (e.g. relative to conventional engineering thermoplastics) are desired, e.g. in low dielectric plastics. These relatively low dielectric plastics are particularly preferred and are preferably achieved by using aromatic compounds substituted with trifluorovinyl groups, most preferably, with trifluorovinyl ether groups. Very low proportions of the perfluorocyclobutane groups result, for instance, when low molecular weight oligomers (e.g. in the range of 1000 to 20,000) are terminated by trifluorovinyl groups which are then thermally dimerized to form higher molecular weight polymers.

Any monomer having at least two dimerizable perfluorovinyl groups is suitably used in the practice of the invention. Whereas polyaddition of perfluorovinyl groups to form perfluoroaliphatic polymers (like polytetrafluoroethylene), not generally having perfluorocyclobutane groups, takes place in the presence of free radicals or free radical generating catalysts, dimerization to form perfluorocyclobutane groups takes place thermally.

When a perfluorovinyl group is dimerizable, dimerization is preferably favored over other thermal reactions either kinetically or in equilibrium. In perfluorobutadiene, isomerization and formation of perfluorocyclobutane is favored: it is, therefore, preferable in the practice of the invention that the perfluorovinyl groups on a monomer used in the practice of the invention be separated by at least one atom or group of atoms, which group does not facilitate isomerization. The atom or group of atoms preferably includes at least one carbon atom, more preferably at least one carbon atom in an, optionally substituted, hydrocarbyl group, that is a group containing at least one carbon-hydrogen bond for instance a methylene group, a phenylene group, a phenylene ether group, a pyridinyl group and the like. Furthermore, when the perfluorovinyl groups are attached to aliphatic carbons or separated from aliphatic carbons by single atoms such as oxygen, the perfluorovinyl groups are preferably primary or secondary because tertiary perfluorovinyl groups are generally sterically hindered with respect to formation of perfluorocyclobutane rings, more preferably the perfluorovinyl groups are primary because secondary perfluorovinyl groups tend to rearrange. Preferably, to avoid rearrangement and facilitate polymer formation the monomers have structures such that resulting polymers have hydrocarbyl groups (preferably aromatic rings), perfluorocyclobutane rings and at least one non-carbon atom such as oxygen, silicon, boron, phosphorus, nitrogen, selenium, tellurium and/or sulfur atom (each optionally substituted) in the backbones.

The monomers preferably have a structure represented by Formula I:

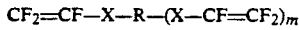

wherein R represents an, optionally inertly substituted group; each X is independently a bond or any group which links R and a perfluorovinyl group (hereinafter linking structures), said structure is independently a bond or any group which links R and a perfluorovinyl group (hereinafter linking structures), said structures being inert; m+1 is the number of —X—CF=CF₂ units. Advantageously, m is an integer of from about 1 to about 3, preferably from about 1 to about 2. While compounds represented by Formula I wherein m is one are especially useful for forming linear polymers, compounds wherein m is 2 or more particularly 2 or 3 are especially useful for preparing crosslinked polymers. By "inert" it is meant that the structures or substituents do not react undesirably with perfluorovinyl groups or interfere undesirably with polymerization (perfluorocyclobutane formation) of the monomers.

Linking structures X are each independently a linking structure such as a bond, an oxygen atom, carboxylic and thiocarboxylic ester groups, other sulfur containing structures, perfluoroalkylene, perfluoroalkylene ether, alkylene, acetylene, phosphorus containing groups such as phosphines, carbonyl and thio carbonyl groups; seleno: telluro: nitrido; silicon-containing groups such as silanediyl, trisilanediyl tetrasilanetetrayl, siloxanediyl, disiloxanediyl, trisiloxyl, trisilazanyl, or silylthio groups; boron-containing groups such as boranediyl or methylboranediyl groups; a combination thereof, or any other group which is inert, which molecularly links R to a perfluorovinyl group, and which provides a molecular structure in which the perfluorovinyl group is sufficiently reactive to form a perfluorocyclobutane ring. For instance, X is preferably other than a perfluoroalkylene group because perfluorovinyl groups attached to perfluoroalkylene groups generally require temperatures greater than about 300° C. to dimerize and are subject to isomerization.

It is preferred that at least one of X is not a bond. More preferably, X is independently selected from the group consisting of groups having at least one noncarbon atom between the perfluorovinyl groups and R, such as groups containing oxygen, sulfur, selenium atoms, tellurium atoms, silicon, boron, phosphorus or nitrogen between R and the perfluorovinyl group, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, O or Si between R and the perfluorovinyl group, such as carbonyl, thiocarbonyl, sulfone, sulfoxy, silanediyl, amines (optionally inertly substituted), oxygen or sulfur atoms. Most preferably there is a single atom other than carbon; even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the perfluorovinyl group is attached directly to R, particularly when R is aromatic. Monomers having such linking structures are also relatively easily prepared.

R is suitably any inert molecular structure, preferably a molecular structure which facilitates formation of perfluorocyclobutane rings and/or imparts desirable physical properties to polymers or oligomers prepared from the monomers. For the purpose of imparting desirable physical properties to polymers, R preferably contains at least one carbon atom. Preferably, the carbon atom is in the molecular chain between X's because monomers having at least one carbon atom between X's when X is other than a bond, tend to have desirable stability and to produce polymers having desirable physical properties. Alternatively, the carbon atom is in a side chain: for instance, —R— can be —N(CH₃)—, —N(CH₂CH₃)—, —P(CH₃)—, —P(CH₂CH₃)— and the like. The carbon atoms(s) in R are suitably in aliphatic, cycloaliphatic, aromatic, heterocyclic groups and the like and combinations thereof. Additionally, R optionally contains groups or has substituents which are inert, that is which do not undesirably interfere with the formation of perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, aromatic, heterocyclic, alkoxyl, aryloxy groups and the like, which inert substituents are suitably in any position, for instance, in a polymer backbone between X's and/or appended to such a backbone. Carbon-containing inert substituents on R preferably contain from about 1 to about 50, more preferably from about 1 to about 12 carbon atoms because of the stability and ease of working with monomers of lower molecular weight. R, including inert substituents preferably has a molecular weight (MW) of from about 14 to about 20,000, more preferably from about 75 to about 15,000 and most preferably from about 75 to about 5,000. These ranges include monomeric and oligomeric R groups. In the case of monomers which are other than oligomeric, R preferably has from about 1 to about 50, more preferably from about 6 to about 50, carbon atoms because molecular weights above this reduce the contribution to properties made by the fluorinecontaining substituents when R is alkyl or aromatic hydrocarbon. As previously discussed, the nature of R as well as the perfluorocyclobutane content of the polymers can vary broadly according to the type of products desired.

Preferably, for polymers having good plastic properties such as tensile strength and flexibility, at least one carbon atom of R is in the molecular chain between X's and is part of an aromatic nucleus. Aromatic groups are desirable because of improved physical properties of the polymers and ease of manufacture of the monomers. For both ease of manufacture of the monomer and monomer stability, when R is aromatic, each X is preferably independently sulfur or oxygen. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—$C_6H_4$—C($CH_3$)$_2$—$C_6H_4$]; p,p'—(2,2-diphenylene-1,1,1,3,3,3 hexafluoropropane) [—$C_6H_4$—C($CF_3$)$_2$—$C_6H_4$—], preferably biphenylene; phenylene: 9,9-diphenylenefluorene, oxydiphenylene: thiodiphenylene; 1,1,1-triphenyleneethane; 1,3,5-triphenylene benzene; 1,3,5-tris(2-phenylene-2-propyl)benzene: 1,1,1-triphenylenemethane: 1,1,2,2-tetraphenylene-1,2-diphenylethane, 1-(2-phenylene-2-propyl)-4-(1,1-diphenyleneethyl)benzene; 2,2-diphenylene propane: 2,2-diphenylene-1,1,1,3,3,3-hexafluoropropane; 1,1-diphenylene-1-phenylethane; naphthalene; and anthracene. Molecular weights of aromatic ring containing polymers are preferably at least about 10,000. Such aromatic groups are preferably present because they generally impart high temperature glass transition properties (Tg) and good mechanical strength (e.g. as measured by differential scanning calorimetry (DSC) and tensile/flexural tests) to the polymer.

Most preferably, at least one aromatic carbon atom of R is bonded directly to X, most preferably aromatic carbon atoms of R are bonded directly to each X because perfluorovinyl groups bonded to X, said X being bonded to aromatic groups are generally more reactive in forming perfluorocyclobutane rings.

Some specific combinations of X and R are especially preferred: when R is aromatic, at least one X is preferably other than a bond, more preferably neither X is a bond, because attachment of perfluorovinyl groups directly to aromatic R renders the perfluorovinyl groups more thermally and oxidatively unstable than when said groups are attached, for instance, to oxygen or sulfur. When R is a perfluoroalkyl group or a perfluoroalkylether group, at least one X is preferably other than a bond, most preferably no X is a bond or a perfluoroalkyl group, because perfluorovinyl groups linked directly to perfluoroalkyl groups require temperature in excess of about 300° C. to dimerize and are subject to isomerization.

Monomers useful in the practice of the invention are suitably prepared by any method which links molecular structures having perfluorovinyl groups to other molecular structures or which forms perfluorovinyl groups.

Perfluorovinyl groups are formed, for instance by elimination of halogens from terminal dihalotrifluoroethyl groups. Halogens such as bromine or iodine may be eliminated, for instance, using metallic reactants as illustrated by Cohen's synthesis of trifluorostyrene by the reaction of zinc with dichlorotrifluoroethylbenzene in absolute ethanol (*J. Am. Chem. Soc.*, 71, 3439, (1949)). Additionally, pentafluoroethyl (substituted) phenyl ethers can be reacted with certain phosphorus compounds to form perfluorovinyl ethers as reported by Kawaguchi et al. in Japanese Kokai 77 89,603. Structures suitable for elimination of halogens to form perfluorovinyl groups are prepared, for instance, by processes such as those taught in Rico et al. U.S. Pat. No. 4,377,711 and Carl et al. in U.S. Pat. No. 4,423,249 which patents are incorporated herein by reference. Additionally perfluorovinyl groups are formed by decarboxylation of perfluorocarboxylic acids with concomitant loss of hydrogen fluoride, as taught by R. N. Griffin and M. I. Bro, *J. Org. Chem.*, 25, 1068 (1960), and also by T. S. Reid, G. H. Smith, and W. H. Pearlson, in U.S. Pat. No. 2,746,997 which are incorporated herein by reference. Electrochemical elimination of halogens from certain substituted alkyl-1,2-dihalo-1,2,2-trifluoroethyl ethers according to the procedures taught in European Patent document EP 293,856 is also useful for forming perfluorovinyl compounds.

Tetrafluoroethylene and chlorotrifluoroethylene are reacted with suitable compounds, for instance by procedures taught by Prober in *J. Amer. Chem. Soc.*, 75, 968 (1953): by Plumer et al. (U.S. Office Saline Water, Res. Develop. Prog. Rep. #481, 1969): by Dixon in *J. Org. Chem.*, 21, 400 (1956); Wall et al. U.S. Pat. No. 3,277,068.

Linking of molecular structures containing perfluorovinyl groups to other molecular structures is illustrated by reaction of (trifluorovinyl)trimethyltin aryl iodides in the presence of palladium complexes, as taught by R. S. Sorokina, et al. in *Zh. Org. Khim.* 18, 2458, (1982); by the reaction of trifluorovinyl zinc reagents with certain substituted phenyl iodides as taught by R. S. Sorokina et al. in *Izv. Akad. Nauk SSSR, Ser. Khim.*, 1647, (1985); and Heinze and Burton in *J. Fluorine Chem.*, 31, 115, (1986), and *J. Org. Chem.*, 53, 2714, (1988).

Preferred monomers are preferably prepared by the process taught in copending application Ser. No. 364,665, filed June 22, 1989, filed simultaneously herewith and incorporated herein in its entirety.

An exemplary method of preparing a trisperfluorovinyl ether (exemplary of monomers having three perfluorovinyl groups) is illustrated by a process having the following steps:

A) A trihydroxy compound such as 1,1,1-tris(4-hydroxyphenyl)ethane is converted to its sodium or potassium salt in a solvent such as a methanol/water mixture The methanol or another solvent for the trihydroxy compound is used when, as in the case of 1,1,1-tris(4-hydroxyphenyl)ethane, the compound is not water soluble. Sufficient alcohol is used to keep the trihydroxy compound in solution; in the case of 1,1,1-tris(4-hydroxyphenyl)ethane from about 20 to about 50 volume percent based on total volume of alcohol and water is convenient. Alternatively, the trihydroxy compound is combined with aqueous sodium or potassium hydroxide and stirred vigorously until salt formation reaches the desired state, advantageously as indicated by dissolution. Salt formation occurs conveniently at from about 0° C. to about 100° C. at atmospheric pressure, preferably under a nitrogen atmosphere to avoid oxidation.

B) The methanol if used is removed under reduced pressure at any convenient temperature and pressure with replacement of water as it is lost.

C) The salt is dried and powdered e.g. in a drum dryer.

D) The salt is slurried in a polar, aprotic solvent suitable for achieving reaction such as DMSO (dimethyl sulfoxide), dioxane, DMF (dimethyl formamide), HMPA (hexamethylphosphoramide), diglyme, tetraglyme or glyme and an aprotic azeotropic medium such as toluene or chlorobenzene in a solvent to azeotropic medium ratio of from about 10 to 1 to about 1.5 to 1 and dried by the azeotropic removal of water.

E) About half of the azeotropic medium is removed, e.g. by distillation and the mixture is cooled below about 50° C., preferably below about 20° C.

F) A dihalotetrafluoroethane such as 1,2-dibromotetrafluoroethane is added to form a mixture as the reaction temperature is controlled at a temperature suitable for the reaction to occur substantially without the side reaction of ring halogenation; in the case of 1,1,1-tris(4-hydroxyphenyl)ethane preferably below about 20° C. initially. The mixture is stirred at 18–25° C. for 36 hours.

G) The mixture is poured into about an equal volume of cold water, conveniently from about 0.5 to about 3 times the volume of the solution, and the product falls out as the lower layer. There is preferably sufficient cooling to offset the heat generated by admixing DMSO (or other solvent) and water.

H) The product, a tris-bromide, is distilled, e.g. at about 190–195° C./0.05 mm Hg. When tris-bromides are heat stable as observed in the case of 1,1,1-tris(4-(2-bromotetrafluoroethoxy)phenyl)ethane, the degree of vacuum is selected to give a convenient boiling point. Such selection is within the skill in the art.

I) The tris-bromide is used directly or, if desired, in cases where the tris-bromide is a solid for ease of addition it may be dissolved in a polar, aprotic solvent such as diglyme, tetraglyme, or glyme and added to a hot (e.g. 120° C.) mixture of the same solvent and granular zinc to form the tris-perfluorovinyl ether (TVE). Alternatively, the tris-bromide can be added to a hot (e.g. 120° C.) mixture of for example, diglyme and granular zinc as a melt without dilution if heated above its melting point, e.g. to about 120° C. in the case of 1,1,1-tris(4-(2-bromotetrafluoroethoxy)phenyl)ethane. Temperatures above about 125° C. are preferably avoided to avoid dimerization of perfluorovinyl groups.

J) The TVE is isolated by removing the zinc salts e.g. by centrifugation, evaporating the diglyme under reduced pressure, diluting the TVE with a, preferably low boiling, solvent such as hexane, and flushing the solution through a pad of neutral alumina. Alternatively, the zinc salts are removed by filtration and the TVE distilled under vacuum, e.g. in two stages, the first to remove solvent and the second to purify the TVE. Preferably, temperatures above about 110° C. are avoided to avoid dimerization of perfluorovinyl groups. Especially when a very pure product is desired, these methods of purification are suitably combined.

K) The hexane, if used, is removed from the TVE by evaporation under reduced pressure.

Alternatively, the TVE is isolated by removing the zinc salts by filtration, evaporating the diglyme under reduced pressure, diluting the TVE with hexane and purifying by countercurrent extraction with polar organic materials such as acetonitrile or DMSO. The pure TVE in hexane is then flushed through a pad of alumina and isolated by concentration under reduced pressure.

The monomers are heated to a temperature and for a time sufficient to form perfluorocyclobutane rings. Temperatures suitable for forming perfluorocyclobutane rings differ with the structure of the monomer. In general, temperatures above about 40° C. are suitable for formation of perfluorocyclobutane rings, preferably the temperature is above about 50° C., more preferably above about 100° C., because these temperatures result in formation of the rings at successively faster rates. Temperatures above about 450° C. are preferably avoided because perfluorocyclobutane groups are generally thermally unstable above such temperatures. More preferably a temperature of from about 105° C. to about 350° C., most preferably from about 105° C. to about 250° C., is used to produce the perfluorocyclobutane rings at a convenient rate. Within that range, a temperature of from about 100° C. to about 230° C. is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. In the case of perfluoroalkylperfluorovinyl groups, however, temperature of at least about 300° C. preferably at least about 350° C., is generally required.

Preferably, especially when the perfluorovinyl compounds are capable of radical initiated addition polymerization, conditions conducive to free radical polymerization, e.g. presence of oxygen, ozone, peroxygen compounds and other free radical generating compounds are avoided so that the perfluorovinyl groups will dimerize into perfluorocyclobutane groups rather than undergoing addition polymerization. Compounds known in the art for stabilization against free radical polymerization are alternatively used. Similarly, especially when the perfluorovinyl groups are capable of addition polymerization in the presence of anions or cations, compounds which supply such anions or cations are avoided. For instance, fluoride ions (e.g. from carbonyl fluorides), chloride, hydroxide, phenoxide and the like are preferably avoided. To avoid such compounds as carbonyl fluorides, oxidative conditions such as presence of oxygen, hypochlorite, dichromate, permanganate and the like are preferably avoided because the perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when such perfluorovinyl compounds are used.

Monomers or admixtures thereof are suitably neat or, optionally, in admixture with other materials such as in solution, in emulsion, in dispersions or in any other form in which monomer molecules can be contacted with one another to form a polymer. Neat polymerization is preferred when the monomers or prepolymers are formed in the final desired shape of the polymer article before final thermal treatment. This is especially true when monomers having more than two perfluorovinyl groups are used in whole or in part to form crosslinked, thermoset materials.

Suitable solvents are those which are inert to the conditions encountered in the polymerization reaction and include xylene, mesitylene and perfluorotetradecahydrophenanthrene (MULTIFLUOR® APF 215 commercially available from Air Products Corp.). At atmospheric pressure, preferred solvents are those which attain temperatures of 170°-250° C. such as dichlorobenzene, trichlorobenzene, diphenyl oxide and perfluorotetradecahydrophenanthrene. Although solvents such as 1,2-dichlorobenzene and 1,2,4-trichlorobenzene give less satisfactory results such as discoloration of the finished polymer, they are suitably used when their disadvantages are tolerable in a final product. When a solvent is used the concentration of monomers in solvent is advantageously from about 0.1 to about 99.9 weight percent preferably, from about 10 to about 90 percent by weight monomer.

Polymerization or dimerization suitably takes place at any pressure. Pressures are generally chosen such that the monomers and any solvents and/or dispersing media remain liquid at the temperatures used for polymerization. When the monomers or other materials evaporate at temperatures used, then it is generally preferable to maintain a pressure at least sufficient to maintain the materials liquid.

Monomers having three or more dimerizable perfluorovinyl groups (hereinafter referred to as polyfunctional) are especially useful to form polymers having relatively high Tg believed to be due to crosslinking. From about 0 to 100 percent by weight of such monomers are suitably used, preferably sufficient of the monomers having at least three perfluorovinyl groups to measurably increase the Tg of the polymer over that of a polymer of monomers having corresponding structures but with only two perfluorovinyl groups, more preferably at least about 0.5 mole percent, most preferably from about 0.1 to about 100 mole percent of such monomers is used. While use of lower proportions of polyfunctional monomer(s) produces generally thermoplastic polymers having crosslinking and corresponding properties of toughness and solvent resistance, use of sufficient polyfunctional monomer to form thermosetting polymers is useful to produce crosslinked polymers having higher Tg. The relative proportions of polyfunctional monomer which produce such polymers varies with the structure of the monomers. However, from about 0.05 to about 75 mole percent polyfunctional monomers used with monomers having 2 perfluorovinyl groups is sufficient to result in sufficient crosslinking in a thermoplastic polymer to reduce its solubility in a solvent. Thermoset polymers, however, are advantageously formed from monomer mixtures having from about 75 to about 100 weight percent, preferably from about 85 to about 100 mole percent, of the polyfunctional monomers. For instance, a polymer of 1,1,1-tris(4-trifluoroethenyloxyphenyl)ethane which is about 97 weight percent pure, with the major impurity being 1,1-bis(4-trifluoroethenyloxyphenyl)-1-(4-(1,1,2,2-tetrafluoroethoxy)phenyl)ethane, is polymerized at about 180-240° C. for 30 min. and produces a colorless, transparent polymer having a Tg of 286° C.

While monomers of the invention are conveniently polymerized in a single stage polymerization, use of more than one stage is often advantageous. A first stage can advantageously be used to react some of the perfluorovinyl groups to reduce the exotherm frequently observed when large quantities of monomers, particularly of monomers having at least three perfluorovinyl groups are polymerized in a single stage. A first stage is also useful to produce a monomer (or monomer mixture of solution) having increased viscosity and lower volatility than those of the initial monomer. A liquid or a solid of relatively lower melting point than that of a completely cured polymer is suitably formed. Such a first stage of polymerization is conveniently carried out at temperatures of from about 50° C. to about 400° C., preferably from about 105° C. to about 250° C., more preferably from about 120° C. to about 170° C. At least one later stage follows the first stage and is preferably carried out at a higher temperature than the first to allow the polymerization to proceed toward completion. Such later stage(s) are conveniently carried out at temperatures from that sufficient to result in additional polymerization up to the decomposition temperature of a resulting polymer, preferably from about 100° C. to about 450° C., more preferably from about 120° C. to about 400° C., most preferably from about 200° C. to about 375° C. Those skilled in the art will recognize that the first and later stages can represent more than one stage or can be carried out using two or more temperatures and that a series of stages or a continuum of temperatures are suitably used. In addition to these stages, a postcure at a relative high temperature such as from about 200° C. to about 450° C. is optionally used. The postcure is suitably of any duration sufficient to change physical properties and insufficient to decompose the polymer, preferably from about 1 minute to about 1 week, more preferably at higher temperatures such as from about 240° C. to about 450° C. for duration of from 1 minute to about 24 hours. Stages of polymerization are conveniently run under conditions previously described for polymerization of the monomers. When a solvent is used in an early stage, and it is desirable to avoid bubbles that may occur as a solvent is driven off, advantageously the solvent removed before or during a later stage.

In a preferred embodiment of the invention, conditions suitable for all or part of the dimerization can occur in a polymer shaping apparatus, for instance, an extruder, injection mold or compression mold. This embodiment of the invention is particularly useful when materials containing perfluorovinyl groups, for instance, monomers, oligomers or polymers, have a viscosity suitable for introducing into the polymer shaping apparatus and the material resulting from the formation of perfluorocyclobutane groups in the apparatus has a higher viscosity or is solid, which is less suitable for introduction into the apparatus. More specifically, a perfluorovinyl containing oligomer or relatively lower molecular weight polymer, including the result of partial dimerization of perfluorovinyl groups is introduced into a shaping apparatus wherein it is heated sufficiently for formation of sufficient perfluorocyclobutane rings to form a solid polymer.

Another preferred embodiment of the present process is to form perfluoropolymers, preferably having ether atoms incorporated in the polymer backbone. Polymers of this general class of compounds are generally prepared by fluoride ion catalyzed reactions of perfluorinated epoxides (U.S. Pat. Nos. 3,214,478 and 3,322,826). These type products have perfluorocyclic groups, including perfluorocyclobutane groups, are taught in U.S. Pat. No. 3,303,145. While the methods taught are suitable for preparing low molecular weight materials, the method is generally unsuitable for producing higher molecular weight products (e.g. average molecular weights at least about 10,000). Elimination of fluoride to form acid fluoride terminal groups in the growing chains generally limits molecular weight. This deficiency can be offset somewhat by lowering reaction temperature, but nevertheless the only commercially significant products produced using a process like that taught in the prior art patents are oligomeric fluids such as Krytox ® commercially available from I. E. DuPont and Company. Formation by the cyclopolymerization process of the present invention makes possible production of higher molecular weight polymers. Preferably perfluoro polymers of this embodiment of the present invention are thermally produced from monomers of Formula I wherein R is perfluoroalkyl, X is oxygen. These monomers are conveniently produced by known chemistry involving reaction of perfluoroalkyl compounds having two acid fluoride groups with fluoropropyl epoxides followed by decarboxylation to form vinyl ethers. (See U.S. Pat. Nos. 3,450,684 and 4,554,112). The resulting monomers, perfluoroalkyl diperfluorovinyl ethers, $CF_2=CFO(CFR_f)_nOCF=CF_2$, where $R_f$ is branched or linear fluoroalkyl (preferably of from about 1 to about 10 carbon atoms), or fluorine; and n is preferably between 1 and about 10, are then thermally polymerized to form polymers, or if desirable, oligomers having the repeating unit,

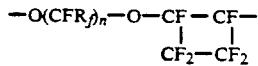

and terminated trifluorovinyl ether groups. The polymers having average molecular weight above about 10,000, preferably above about 25,000 are useful in elastomer applications, particularly when cured by a crosslinking reagent. Suitable crosslinking reagents are monomers described herein where m is greater than 1. The terminal groups are conveniently further reacted, if desired, by a variety of processes within the skill in the art including radical initiated reactions or, alternately, are rendered inert by halogenation, preferably with fluorine. It is within the scope of the present invention to copolymerize the foregoing monomers, oligomers or polymers with other compounds of the present invention having two or more trifluorovinyl groups. For instance, oligomers of the divinylperfluoroethers are formed and cured with a perfluorovinyl compound, particularly of Formula I wherein R is aromatic, m is 2 and both X's are oxygen. This technique is useful for forming thermoset resins or elastomers depending on the proportion of multifunctional (m greater than 1) material used.

Polymers of the invention are suitably solids, fluids or gels, preferably solids or fluids, most preferably solids. The solids preferably maintain plastic characteristics such as tensile strength well above ambient temperatures (e.g. above about 25° C.) and have glass transition temperatures from well below ambient to well above ambient temperatures. A particularly preferred group of such polymers have glass transition temperatures (Tg) above ambient (25° C.), preferably above 60° C. and most preferably above 100° C. In general, the polymers having Tg above ambient result from monomers of Formula I wherein R is aromatic, and the polymers having Tg above 60° C. when R contains more than one aromatic ring. A particular desirable property of polymers where R is aromatic and not substituted with polar substituents (e.g. nitro, sulfonate, carboxy) is the combination of good physical properties and good electrical properties. Dielectric constants and static dissipation factors (as measured according to the procedures of ASTM D150-87) preferably range from about 2.2 to about 3.0 and from about 0.0001 to about 0.005 respectively. Glass transition temperatures increase from about ambient when R is phenyl to about 170° C. when R is biphenyl to 230° C. when R is 9,9-diphenylfluorene, to about 286° C. or higher when R is 1,1,1-triphenylethane.

The linear polymers are advantageously thermoformed as by molding or extruding or are cast from solvents such as ethers and chlorinated solvents, for instance, tetrahydrofuran or dichloromethane. The polymers possess processing advantages over other polymers having similar low dielectric properties such as polytetrafluoroethylene. The advantages include extrudability, suitability for injection molding, and solvent casting.

The following examples are offered to illustrate but not to limit the invention. In each case, percentages are weight percent unless otherwise indicated. Examples (Ex.) of the invention are indicated numerically, while comparative samples (C.S.) are not examples of the invention and are indicated with letters.

All gas chromatography/mass spectrometry (GC/MS) analyses of monomers and intermediates are performed on a Finnigan 1020 GS/MS using a 30 meter RSL-150 fused silica capillary column. All gas chromatography/mass spectrometry (GC/MS) analyses of fluid polymer samples are performed on a Finnigan 4500 GC/MS using a 60 meter DB-1 fused silica capillary column, with the GC program run at 290° C. isothermal. Mass to charge (m/e) ratios and percentage of peak height relative to tallest (parent) peak are given.

Differential scanning calorimetry (DSC), thermomechanical analysis (TMA) and thermogravimetric analysis (TGA) are performed on a Perkin Elmer 7000 thermal analysis system unless otherwise indicated.

Dielectric constant and dissipation factor measurements are conducted according to the procedures of ASTM D150-87. Tensile strength and modulus and percent elongation were measured on an Instron model 1125 according to the procedures of ASTM D 882-83.

Granular zinc is activated by washing in 0.1 N hydrochloric acid (HCl) followed by drying in a vacuum oven at 0.5 torr and 140° C. for 10 hours.

Infrared (IR) spectra are measured on a Beckman Microlab 600 model spectrophotometer. Nuclear Magnetic Resonance (NMR) spectra are measured on a Varian EM360L spectrometer using 19F (fluorine 19) or 1H (hydrogen) mode.

EXAMPLE 1

Preparation of 1,1,1-tris(4-trifluoroethenyloxyphenyl) ethane and Bulk Polymerization Thereof with 4,4'-bis(trifluoroethenyloxy) Biphenyl A 1 liter 5-necked round bottom flask is fitted with a mechanical stirrer, a Dean Stark trap topped with a nitrogen padded reflux condenser, and a thermocouple attached to a temperature controller. A mixture of DMSO (450 ml), toluene (150 ml), and 1,1,1-tris(4-hydroxyphenyl)ethane (55.1 g, 0.18 mole) is added to the flask under nitrogen purge. After stirring for 15 minutes under a vigorous nitrogen purge, potassium hydroxide (85% pellets, 80.0 g, 1.2 mole) is slowly added to the reaction flask. The mixture is then stirred at reflux for 48 hours with azeotropic removal of water. The resulting suspension is cooled to 35° C. in an ice bath and 1,2-dibromotetrafluoroethane (155 g, 0.60 mole) is added at a rate that maintains a temperature of 30°-35° C. When the addition is complete, the mixture is heated to 50° C. with continuous stirring for 3 hours. After filtration, the solvents are removed by heating under vacuum on a rotary evaporator. The brown residue is purified by column chromatography on neutral alumina using hexane as eluent to provide as product 1,1,1-tris(4-[2-bromotetrafluoroethoxy]phenyl)ethane (18.3 g, 0.022 mole, 12% yield).

Identity of the product is confirmed by a GC/MS spectrum, the following peaks; m/e: parent ions m/e 840-842-844-846 (ratio 1:3:3:1) too heavy to detect. Structure determined from fragmentation: 573 (32.3%); 571 (58.3%); 569 (31.5%); [indicating parent—PhOCF$_2$CF$_2$Br]). 299 (58.1%); 297 (52.7%); 279 (32.3%); 228 (43.5%); 227 (31.5%); 226 (36.0%); 215 (59.5%); 181 (82.1%); 179 (100.0%); 165 (50.3%); 152 (43.7%); 131 (47.1%); 129 (50.4%); 100 (38.8%).

Into a 500 ml 5-necked flask fitted with a mechanical stirrer, a reflux condenser, and a thermocouple attached to a temperature controller is placed freshly activated granular zinc (4.3 g, 0.066 mole) and 25 ml dry diglyme. This mixture is stirred and heated to 110° C. under nitrogen while the product from the above reaction (18.0 g, 0.021 mole) is dissolved in 21 ml diglyme and added dropwise. The resulting mixture is stirred at 115° C. for 3 hours, then cooled and filtered. The filtrate is evaporated at 60° C. under vacuum to remove the diglyme, and the residue is purified by column chromatography on neutral alumina using hexane as eluent to provide the product 1,1,1-tris(4-trifluoroethenyloxyphenyl)ethane (9.98 g, 0.018 mole, 87% yield).

The GC/MS spectrum has the following peaks: m/e: 546 (3.2%); 531 (44.0%); 434 (17.9%); 373 (24.4%); 276 (16.9%); 240 (28.1%); 239 (73.9%); 199 (19.3%); 178 (100.0%); 177 (17.8%); 176 (25.4%); 163 (17.3%); 152 (31.9%); 151 (17.8%); 127 (20.3%); 126 (28.7%); 120 (39.1%); 119 (70.3%); 118 (25.6%); 113 (27.3%); 107 (18.8%); 102 (31.7%); 77 (15.9%); 76 (29.5%).

This example illustrates preparation of a trifunctional monomer, 1,1,1-tris(4-trifluoroethenyloxyphenyl)ethane. This monomer is useful alone or mixed with a bifunctional monomer to produce a crosslinked perfluorocyclobutane polymer.

4,4'-bis(trifluoroethenyloxy)biphenyl is prepared according to the following procedure:

Dimethyl sulfoxide (DMSO) (1800 ml) is placed in a 5-liter 5-necked flask fitted with a mechanical stirrer, a Dean-Stark phase separating trap topped with a nitrogen padded reflux condenser, and a thermocouple attached to a temperature controller. The solvent is stirred and purged of oxygen by blowing in nitrogen through a dip-tube placed below the surface of the liquid while 4,4'-dihydroxybiphenyl (454 g, 2.44 mole) is added to the flask.

The system is stirred and purged for 20 minutes, then potassium hydroxide (85% pellets) (322 g, 4.88 mole) is added slowly. The stirred mixture is then heated to 120° C. The temperature is held at 120° C. for 1.5 hours, then the heat is turned off and the mixture is allowed to cool to room temperature. Toluene (600 ml) which has been thoroughly purged with nitrogen is added to the solution and the resulting mixture is heated to reflux (135° C.). Water is axeotropically removed from the reactor through the Dean-Stark trap for a total of 4 days, cooling the reactor once after 24 hours to allow for salt formation to be broken up by opening the flask under a nitrogen sweep and scraping the sides with a spatula. After 4 days the Dean-Stark trap is removed and replaced with a Soxhlet extractor containing anhydrous sodium sulfate. The toluene is then refluxed through the Soxhlet extractor for 7 hours to dry the toluene. After 7 hours, the Soxhlet is replaced with a Dean-Stark trap, and toluene (300 ml) is removed from the reactor by simple distillation. The reaction mixture is then cooled to 30° C. in an ice water bath and 1,2-dibromotetrafluoroethane (1300 g, 5.00 mole) is added slowly dropwise over three hours at a rate that maintains a reactor temperature of 35°±2° C. When the addition is complete the reaction temperature is allowed to stabilize (not increasing in temperature when the ice bath is removed) and then a heating mantle is applied to the flask. The reactor is heated to 50° C. for 8 hours, then allowed to cool to room temperature with constant stirring. The crude reaction mixture is filtered to remove the potassium bromide salts, and the precipitate is washed with acetone. The filtrates are combined and thoroughly evaporated to remove acetone, DMSO and residual toluene. The solid residue is subjected to a 2 liter Kugelrohr bulb-to-bulb distillation to provide the crude product. This material is dissolved in 750 ml of methylene chloride and is washed first with mild aqueous potassium bicarbonate (500 ml, approximately. 0.2M), then with mild aqueous hydrochloric acid (HCl) (500 ml, approximately 0.05M), then twice with distilled water (500 ml each). After complete phase separation the product layer is removed and evaporated, and the residue is fractionally distilled (138°-148° C., 0.35 torr) to provide 1031.1 g (1.90 mole, 77.9% yield) of 4,4'-bis(2-bromotetrafluoroethoxy)biphenyl, melting point 71°-73° C. The Infrared (IR) spectra of the product has the following peaks (cm$^{-1}$); 1601,1492 (indicating an aromatic double bond); 1199-1107 (indicating carbon-oxygen and carbon fluorine bonds), 842, 788 (indicating aromatic character). The gas chromatograph/mass spectrometer (GC/MS) indicates peaks at the following mass to charge ratios (m/e)=545 (29.8%); 543 (48.9%); 541 (23.8%); 365 (48.7%); 363 (50.9%); 337 (30.3%); 335 (34.7%); 168 (33.7%); 156 (78.3%); 140 (36.7%); 139 (90.1%); 129 (37.4%); 128 (100.0%); 127 (33.2%); 102 (32.9%); 76 (41.1%); 63 (34.3%), consistent with a product of 4,4'-bis(2-bromotetrafluoroethoxy)biphenyl.

Bromine is eliminated from this product by the following procedure:

Into a 1-liter 5-necked flask equipped with a mechanical stirrer, a thermocouple attached to a temperature controller, a powder addition funnel and a reflux condenser, is placed freshly distilled diglyme (200 ml) and fresh zinc powder (36.0 g, 0.55 mole).

The mixture is stirred and heated to 130° C. Powdered 4,4'-bis(2-bromotetrafluoroethoxy)biphenyl (100 g, 0.184 mole) is added very slowly via the powder addition funnel over 3.5 hours. The mixture is then stirred mechanically at 115° C. for 1 hour, after which heating is turned off and the mixture is allowed to cool to room temperature. The solution is centrifuged to remove the zinc salts. Then the liquid is decanted, and the zinc salts are washed with acetone and centrifuged again. The liquid portions are combined and evaporated thoroughly, and the residue is dissolved in methylene chloride and washed with 0.05M hydrochloric acid. The methylene chloride solution is evaporated to provide 62.45 g (0.180 mole) of 4,4'-bis(trifluoroethenyloxy)biphenyl of 94.5% purity in 98% yield.

The product is then recrystallized in an ethanol/water mixture to give product of 99.8% purity in greater than 70% recovery, melting point 44°-46° C.

The IR spectrum shows peaks at (cm$^{-1}$): 1833 (indicative of a perfluorovinyl group); 1601, 1491 (indicative of an aromatic double bond); 1231, 1196-1132 (indicative of carbon-oxygen and carbon-fluorine bonds respectively); 818 (indicative or aromaticity).

The GC/MS spectrum has the following peaks: m/e: 346 (31.3%); 153 (13.8%); 152 (100.0%); 151 (27.0%); 150 (11.7%); 76 (14.9%); 63 (14.9%).

A mixture of the 4,4'-bis(trifluoroethenyloxy)biphenyl (4.50 g, 0.013 mole) and the 1,1,1-tris(4-trifluoroethenyloxyphenyl)ethane (0.79 g, 0.0014 mole) are combined in a 100 ml single necked round bottomed flask topped with a nitrogen padded reflux condenser. The flask is purged thoroughly with nitrogen, and the mixture is heated without stirring. After reaching a temperature of 200° C., the mixture sets into a rigid plastic within 15 minutes. This material is then cured an additional 40 minutes at 220° C.; then the heat is removed. The resulting plastic is rigid, inflexible and does not dissolve in tetrahydrofuran (THF) or methylene chloride, but swells into a gel in these solvents.

DSC analysis (25°-350° C., 20° C./min.) of this polymer sample shows a slight endothermic event at 125° C. followed by a broad exotherm beginning at about 210° C., indicative of an incompletely cured polymer. After this sample is cured during the first DSC scan, a second scan is run which clearly indicates a Tg transition at 151° C. and no subsequent exothermic activity at higher temperatures.

Example 1 illustrates preparation of 1,1,1-tris(4-trifluoroethenyloxyphenyl)ethane and copolymerization 4,4'-bis(trifluoroethenyloxy)biphenyl therewith. The resulting polymer is stiff and brittle, as well as insoluble, compared to a thermoplastic prepared from 4,4'-bis(trifluoroethenyloxy)biphenyl alone, which is flexible and soluble in THF and methylene chloride.

EXAMPLE 2

Bulk Polymerization of 4,4'-bis(trifluoroethenyloxy)biphenyl with Subsequent Addition of 1,1,1-tris(4-trifluoroethenyloxyphenyl)ethane Monomer 4,4'-bis(trifluoroethenyloxy)biphenyl (16.2 g, 0.047 mole) prepared as in Example 1 is placed in a 500 ml round bottom flask along with a magnetic stirring bar. A nitrogen padded reflux condenser is placed on the flask, and the monomer is heated at 200°-205° C. with stirring for 20 minutes, to form a low molecular weight polymer resembling a thick fluid at 200° C. The fluid is allowed to cool to room temperature where it sets into a brittle glass. The glass is dissolved in methylene chloride and 1,1,1-tris(4-trifluoroethenyloxyphenyl)ethane (0.51 g, 0.00094 mole) prepared as in Example 1 is added to the solution. The methylene chloride is evaporated and the residue is dried and devolatilized on a Kugelrohr bulb-to-bulb apparatus at 120-140° C. and 0.20 torr pressure. While still hot, the fluid mixture is poured into a mold and cured on a hot press at 250° C. and 20,000 psi for one hour. The mold is removed from the press and cooled. A coupon is removed from the mold. The coupon is a strong and flexible plastic, and does not dissolve in THF but swells into a gel therein.

DSC analysis of this crosslinked polymer sample indicates a Tg value of 149° C., with no subsequent thermal activity up to and including 350° C.

Example 2 illustrates polymerization of 4,4'-bis(trifluoroethenyloxy)biphenyl with subsequent addition of 1,1,1-tris(4-trifluoroethenyloxyphenyl)ethane. It is notable that crosslinked polymers are prepared either by copolymerizing difunctional and multi-functional monomers, as in Example 1, or by combining a multifunctional monomer with a low molecular weight polymer containing trifluorovinyl end groups as in Example 2.

EXAMPLE 3

Synthesis and Polymerization of 1,1,1-tris(4-trifluoroethenyloxyphenyl)ethane

Potassium hydroxide (678.72 g, 10.28 mol, 85%) is dissolved with cooling into 630 mL of water in a 5 liter round-bottomed flask fitted with a thermometer and stirrer. Methanol (400 mL) is added and the mixture is stirred under nitrogen in an ice bath as a solution of THPE [1,1,1-tris(4-hydroxyphenyl)ethane] (1051 g, 3.43 mol) in 1650 mL of warm methanol (40° C.) is added. Methanol is then removed from the resulting solution of the potassium salt of THPE in water/methanol by distillation under reduced pressure (140 mmHg, 55-60° C.) with addition of a total of 1245 mL of water to make up for losses and to obtain a solution of THPE potassium salt in water with the consistency of light syrup. The potassium salt of THPE is isolated by evaporation of this water solution (48% solids by weight) in a drum dryer. The resulting dried THPE salt contains about 4% water by weight.

The dried THPE salt is transferred to a 12 L round-bottomed flask fitted with a condenser and water trap along with 5 L of dimethysulfoxide (DMSO) and 1.5 L of toluene. This slurry is stirred and heated to reflux under nitrogen to remove residual water by azeotroping it with toluene. After 6 hours of reflux no further water collection is seen in the water trap and the water trap is replaced with a Soxhlet extractor containing dry sodium sulfate. The mixture is refluxed through the Soxhlet extractor for a total of 5.5 h with the sodium sulfate being replaced with an equivalent amount of dry sodium sulfate once at the halfway point, during this process. About 1 L of toluene is then removed by distillation and the remaining mixture is cooled to 18° C. by means of an internal cooling coil containing either tap water or chilled glycol as needed. The temperature of the stirring mixture is maintained at 16-18° C. by means of this internal cooling coil as 1,2-dibromotetrafluoroethane (3000 g, 11.54 mol, 1382 mL) is added over 1 h and the resulting mixture is stirred at 18° C. for 36 hours (h).

The reaction is worked up by pouring the mixture into an equal volume of cold water with stirring and then allowing the layers to separate. The lower layer containing the product is drained and the upper aqueous layer is washed with hexane. The hexane wash is combined with the product layer and evaporated under reduced pressure to remove solvents. The crude product solidifies into a crystalline mass melting at ca. 100° C. This mass is melted and distilled at reduced pressure (190-195° C., 0.05 mm Hg) to yield the product, 1,1,1-tris(4-(2-bromotetrafluoroethoxy)phenyl)ethane, as a yellowish viscous oil which crystallizes upon standing. The yield of this reaction is 88.1% and the product is 93% pure with the remaining 7% being the byproduct 1,1,-bis(4-(2-bromotetrafluoroethoxy)phenyl)-1-(4-(1,1,2,2-tetrafluoroethoxy)phenyl)ethane which results form the replacement of one of the bromine atoms of the product with a hydrogen atom. The byproduct may be removed by melting the distilled crystalline mass and pouring it into an equal volume of methanol with stirring. The product preferentially crystallizes into fluffy white needles which can be filtered from the methanol solution. Alternatively, the 93% pure product may be used directly in the dehalogenation reaction. The crystalline 1,1,1-tris(4-(2-bromotetrafluoroethoxy)phenyl)ethane is found to have the following properties:

White needles, m.p. 100° C.

F-19 NMR: delta −10.4 (t, J=6 Hz, which is attributed to —CF$_2$BR), 7.5 (t, J=6 Hz, which is attributed to OCF$_2$)

H-NMR: delta 2.2 (bs, 3 H), 7.1 (bs, 12 H)

IR: cm−1 1501, 1329, 1312, 1206, 1173, 1126, 1100, 1012, 929, 784

Granular zinc (213.3 g, 3.26 mol, 10-20 mesh) is weighed into an oven-dried 3 L round-bottomed flask. The flask is then fitted with a stirrer, thermometer, septum, and a 1 L pressure-equalizing addition funnel containing 1,1,1-tris(4-(2-bromotetrafluoroethoxy)phenyl)ethane (833.7 g, .989 mol, 97% purity). Dry diglyme (1045 g, 1115 mL) is added to the flask via canula and also to the addition funnel (384 g, 410 mL). The septum is replaced with a stopper, and the zinc/diglyme slurry is stirred and heated to 115° C. as the contents of the addition funnel are heated by means of heating tape to ca. 80° C. to form a homogeneous solution. The solution of 1,1,1-tris(4-(2-bromotetrafluoroethoxy)phenyl)ethane in diglyme is added slowly to the hot stirring zinc/diglyme slurry over 2 h, maintaining the reaction temperature at 115-125° C. by varying both heating rate and rate of addition. After addition is complete the mixture, which now contains precipitated zinc salts, is heated at 120-125° C. for an additional 5 h. The mixture is allowed to cool and the precipitated zinc salts are removed by centrifugation. Ethyl acetate is used to rinse the flask.

The resulting diglyme solution of the tris-perfluorovinyl ether product, 1,1,1-tris(4-trifluoroethenyloxyphenyl)ethane, is concentrated under reduced pressure by rotary evaporation and the resulting mixture of product and zinc salts is slurried in hexane and flushed through a 6"×6" column of neutral alumina commercially available from Aldrich Chemical Company under the trade designation Brockmann I. The product is isolated by evaporation of the hexane solution under reduced pressure. The product is isolated as a colorless oil (yield 85-90%, 89-97% purity). The remainder of the material (7-10%) is a bis-perfluorovinyl ether, 1,1,-bis(4-trifluoroethenyloxy)phenyl)-1-(4-(1,1,2,2-tetrafluoroethoxyphenyl)ethane.

The bis-perfluorovinyl ether is removed by countercurrent extraction to obtain up to 99.9% pure tris-perfluorovinyl ether. A countercurrent extractor is constructed form PFA (Perfluoroalkoxy) tubing (1 in. i.d., 4 ft. length) packed with stainless steel packing, commercially available from Metex Corp. under the trade designation Goodloe ™, two electronic pumps commercially available from Pennwalt Corp. under the trade designation CHEMPULSE ™ (Pennwalt model #45-050-K1M), two solvent reservoirs filled respectively with mutually saturated hexane and acetonitrile, and two receivers.

A sample of impure tris-perfluorovinyl ether ("tris") (180.8 g, 93.5% tris-, 6.5% bis-perfluorovinyl ether; purity as determined by gas chromatography corresponding to mole percent) is diluted with 1500 mL of hexane to make an approximately 10% (by volume) solution. The pumps are started, with hexane pumped into the bottom of the column (above the acetonitrile take-off) and acetonitrile pumped into the top of the column (below the hexane take-off). The flow rates are adjusted to 90 mL/min for hexane and 45 mL/min for acetonitrile. The hexane reservoir is allowed to drain until nearly empty, and the solution of impure tris-perfluorovinyl ether is transferred to the reservoir. After this is transferred onto the column, the reservoir is filled again with 1500 mL of hexane (saturated with acetonitrile). This is allowed to pump through the column and into the product reservoir to ensure complete washing of the product from the column. The hexane solution which exits the column contains tris-perfluorovinyl ether (99.5% purity, 49% recovery). The acetonitrile solution which exits the column contains the remainder of the product (88.35 g, 85.5% tris- and 14.5% bis-perfluorovinyl ether) and is concentrated by rotary evaporation, rediluted in hexane (750 mL) and purified by running it through the countercurrent extractor to give 50.55 g of tris-perfluorovinyl ether (98.2% purity). The acetonitrile solution from this pass contains 25.7 g of material which is 71% tris- and 28.5% bis-perfluorovinyl ether. The ether is found to have the following properties:

1,1,1-tris(4-trifluoroethenyloxyphenyl)ethane:

Colorless, mobile oil

F-19 NMR: delta 42.7 (dd, J(cis)=60 Hz, J(gem)=100 Hz, which is attributed to =CF (terminal vinyl fluorine), cis to F; 49.3 (dd, J(trans)=120 Hz, J(gem)=100 Hz, which is attributed to =CF, trans to F; 55.3 (dd, J(cis)=60 Hz J(trans)=120 Hz, which is attributed to OCF groups)

H-NMR: delta 2.1 (bs, 3 H), 6.95 (bs, 12 H)

IR: cm−1 1830 which is attributed to (CF=CF$_2$) groups, 1500, 1313, 1273, 1205, 11781, 1138, 1011

The 1,1,1-tris(4-trifluoroethenyloxyphenyl)ethane polymerizes at 140-350° C., with a peak exotherm at 235° C.

A polymer is prepared by degassing a 9 g. sample of the 97.5% pure product obtained before purification. 1,1,1-tris(4-trifluoroethenyloxyphenyl)ethane is held under vacuum until no visible bubbles form at room temperature, then heated to 150-160° C. for 2 hours. The sample is then allowed to cool to room temperature. The sample is a solid which is then chipped out of its container and ground into a powder using mortar and pestle. The powder is poured into a mold measuring about 4×5×1/32 inches (10.2×12.7×0.008 cm), put in a press, and compression molded at 240° C. and 10,000 psi (pounds per square inch on the gauge) for 15 minutes. A resulting plaque is removed without cooling and is observed to be clear, flexible and colorless. The polymer is found to have a Tg of 282.1° C. as measured by thermomechanical analysis (TMA) Mettler TA 3000.

EXAMPLE 4

Polymerization of 1,1,1-tris(4-trifluoroethenyloxyphenyl) Ethane

A 30 g sample of the material prepared in Example 3 which is 99.5% pure 1,1,1-tris(4-trifluoroethenyloxyphenyl)ethane is filtered and poured into a vertical casting mold measuring 3×4×1/8 inches (7.6×10.2×0.3cm). The mold is placed in a vacuum oven at 140-160° C. for a period of 2 hours after which, the heat is increased to 240-250° C. for a period of 1 hour. The heat is turned off and the mold allowed to cool to room temperature. The molded polymer is removed and found to have the following properties:

Colorless, transparent Tg (as measured by Thermomechanical Analysis on a Mettler TA 3000)=300° C.; Dielectric Constant (as measured by the procedure of ASTM D150-87)=2.45 (1 MHz) Dissipation Factor (as measured by the procedure of ASTM D150-87)=0.0005 (1 MHz). Upon postcuring by heating twice from 250° C. to 360° C. at a rate of 10° C. per minute, a Tg of 414° C. is obtained.

EXAMPLE 5

Polymerization of 1,1,1-tris(4-trifluoroethenyloxyphenyl) Ethane

The procedure of Example 3 is repeated obtaining a samples of 1,1,1-tris(4-trifluoroethenyloxyphenyl)ethane having a purity of 97 mole percent after having been flushed through alumina using hexane.

A sample of the 97 percent pure 1,1,1-tris(4-trifluoroethenyloxyphenyl)ethane is poured into a compression mold and heated to 160° C. for a period of 2 hours then 240° C. for a period of 30 minutes, after which it is cooled to 25° C. and removed from the mold. The resulting polymer is found a Tg of 286.1° C. and a dielectric constant as determined (as measured by the procedure of ASTM D150-87) of 2.55 and dissipation factor (as measured by the procedure of ASTM D150-87) of 0.001 (1 Megahertz (MHz).

EXAMPLES 6-10

Polymerization of 1,1,1-tris(4-trifluoroethenyloxyphenyl) Ethane

The procedure of Example 3 is repeated obtaining samples of 1,1,1-tris(4-trifluoroethenyloxyphenyl)ethane having the following purities after the steps indicated in Table 1.

Each sample is poured into a pan and put into a vacuum oven at 140° C. for a period of 2 hours, after which the temperature is raised to 240° C. for a period of 1 hour. The pan is removed from the oven and the resulting polymer is cooled to room temperature and removed from the pan. By TMA using a Mettler TA 3000 System, the samples are found to have the Tg's indicated in Table 1.

| Step No. | Step | Purity Mole Percent* | Tg °C. |
| --- | --- | --- | --- |
| 6 | catalyst and solvent (hexane) removal | 89.6 | 276 |
| 7 | counter current extraction using hexane/acetonitrile, first cut in hexane | 99.8 | 300 |
| 8 | recovery from acetonitrile without further purification | 73.6 | 242 |
| 9 | acetonitrile sample after purification by second extraction in hexane | 85.9 | 251 |
| 10 | recovery from acetonitrile portion of hexane extraction of Step 8 | 50 | 178 |

*as determined by gas chromatography

During TMA analysis, Examples 8 and 10 are observed to soften, indicative of thermoplastic character. Examples 6, 7 and 9 are observed to undergo a change in rate of expansion indicative of thermoset character.

These examples show that various purities of tris-perfluorovinyl monomers are obtained using various purification methods and that Tg increases with percentage of polyfunctional monomer. Counter current extraction is particularly useful for removing such impurities as bis-perfluorovinyl ethers. With such extractions, tris-perfluorovinyl monomers exceeding 99.9 percent in purity are obtained and are particularly useful, for instance in electronics applications. Generally such counter current solvent extractions require two solvents which are substantially immiscible, one of which preferentially dissolves the desired product. Solvent combinations useful for the separation in the practice of this invention include solvents for the desired monomer paired with solvents in which the monomer is less soluble, but in which at least some of the impurities are more soluble. Such solvent pairs include hexane/acetonitrile, hexane/dimethysulfoxide, and hexane/dimethylformamide.

Alternatively, the monomers are suitable for polymerization after preparation without purification, preferably with removal of solvent(s) used in preparation. Such monomers in combination with by-products of their preparation are suitable, for instance, for applications wherein lower Tg's are suitable such as molded objects.

What is claimed is:

1. A process for preparing a polymer having perfluorocyclobutane rings comprising the steps of:
   (a) contacting monomers having at least two dimerizable perfluorovinyl groups; and
   (b) exposing the monomers to sufficient heat and for a sufficient time that a polymer containing perfluorocyclobutane rings is formed wherein at least about 0.05 mole percent of the monomers have at least three dimerizable perfluorovinyl groups.

2. The process of claim 1 wherein the monomers are heated to a temperature of at least about 50° C.

3. The process of claim 2 wherein the monomers have at least one atom between dimerizable perfluorovinyl groups.

4. The process of claim 3 wherein the atom is a carbon atom.

5. The process of claim 3 wherein the monomers also have at least one aromatic molecular fragment.

6. The process of claim 5 wherein the atom is oxygen or sulfur.

7. The process of claim 5 wherein the aromatic molecular fragment has from about 6 to about 50 carbon atoms.

8. The process of claim 7 wherein the aromatic molecular fragment has more than one aromatic ring.

9. The process of claim 7 wherein the aromatic molecular fragment is selected from the group consisting of 4,4'-biphenylene; phenylene; 9,9-diphenylenefluorene; oxydiphenylene; thiodiphenylene; 2,2-diphenylenepropane; 1,1,3,3-hexafluoro-2,2-diphenylenepropane; 1,1-diphenylene-1-phenylethane; 1,1-1-triphenyleneethane; 1,3,5-triphenylene benzene; 1,3,5-tris(2-phenylene-2propyl)benzene; 1,1,1-triphenylenemethane; 1,1,2,2-tetraphenylene-1,2-diphenylethane, 1-(2-phenylene-2-propyl)-4-(1,1-diphenyleneethyl)benzene; naphthalene; and anthracene.

10. The process of claim 7 wherein the monomers are heated to a temperature of at least about 100° C.

11. The process of claim 7 wherein the temperature is from about 125° C. to about 350° C.

12. The process of claim 10 wherein the monomers are heated to a first temperature and for a time sufficient to increase viscosity of the monomers, then heated to a second higher temperature and for a time sufficient to result in a crosslinked polymer.

13. The process of claim 12 wherein the first temperature is from about 50° C. to about 400° C. and the second temperature is from about 100° C. to about 450° C.

14. The process of claim 13 wherein the first temperature is from about 105° C. to about 250° C. and the second temperature is from about 120° C. to about 400CC.

15. The process of claim 1 wherein from about 0.5 to about 100 mole percent of the monomers have at least three dimerizable perfluorovinyl groups.

16. The process of claim 1 wherein from about 0.05 to about 75 mole percent of the monomers have at least three dimerizable perfluorovinyl groups.

17. The process of claim 1 wherein from about 75 to about 100 mole percent of the monomers have at least three dimerizable perfluorovinyl groups.

18. The process of claim 17 wherein from about 85 to about 100 mole percent of the monomers have at least three dimerizable perfluorovinyl groups.

* * * * *